(12) United States Patent
Duerk et al.

(10) Patent No.: US 10,646,594 B2
(45) Date of Patent: May 12, 2020

(54) DEUTERATED METABOLIC WATER PRECURSOR FOR DETECTING AND TREATING DISEASED TISSUE

(75) Inventors: Jeffrey L. Duerk, Avon Lake, OH (US); Christopher A. Flask, Avon Lake, OH (US); Gheorghe D. Mateescu, Lakewood, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 265 days.

(21) Appl. No.: 12/819,750

(22) Filed: Jun. 21, 2010

(65) Prior Publication Data

US 2010/0322865 A1     Dec. 23, 2010

Related U.S. Application Data

(60) Provisional application No. 61/218,732, filed on Jun. 19, 2009.

(51) Int. Cl.
*A61K 49/10*     (2006.01)

(52) U.S. Cl.
CPC .................. *A61K 49/10* (2013.01)

(58) Field of Classification Search
None
See application file for complete search history.

(56) References Cited

U.S. PATENT DOCUMENTS

| 2004/0115131 A1* | 6/2004 | Hellerstein | G01N 33/58 424/1.73 |
| 2006/0280682 A1* | 12/2006 | Hellerstein | 424/9.1 |

OTHER PUBLICATIONS

Palm F. Intrarenal oxygen in diabetes and a possible link to diabetic nephropathy. 2006 Clin. Exp. Pharmacol. Physiol. 33: 997-1001.*

Mohanty P, Hamouda W, Garg R, Aljada A, Ghanim H, Dandona P. Glucose challenge stimulates reactive oxygen species (ROS) generation by leucocytes. 2000 J. Clin. Endocrinol. Metab. 85: 2970-2973.*

Hoekstra CJ, Paglianiti I, Hoekstra OS, Smit EF, Postmus PE, Teule GJ, Lammertsma AA. Monitoring response to therapy in cancer using [18F]-2-fluoro-2-deoxy-D-glucose and positron emission tomography: an overview of different analytical methods. 2000 Eur. J. Nucl. Med. 27: 731-743.*

Lou M, Zhang H, Wang J, Wen SQ, Tang ZQ, Chen YZ, Yan WQ, Ding MP. Hyperbaric oxygen treatment attenuated the decrease in regional glucose metabolism of rats subjected to focal cerebral ischemia: a high resolution positron emission tomography study. 2007 Neuroscience 146: 555-561.*

Eskey et al. 2H-nuclear magnetic resonance imaging of tumor blood flow: spatial and temporal heterogeneity in a tissue-isolated mammary adenocarcinoma. 1992 Cancer Res. 52: 6010-6019.*

Golman et al. Real-time metabolic imaging. 2006 Proc. Natl. Acad. Sci. USA 103: 11270-11275.*

Mateescu et al. In vivo 17O magnetic resonance spectroscopy. Determination of temperature effects on metabolic rates (Q10 factor). 1997 Adv. Exp. Med. Biol. 411: 585-590.*

Aguayo, James B., "High Resolution Deuterium NMR Studies of Bacterial Metabolism", The Journal of Biological Chemistry, vol. 263, No. 36, Issue of Dec. 25. pp. 19552-19557, 1988.

* cited by examiner

*Primary Examiner* — Jennifer Lamberski
(74) *Attorney, Agent, or Firm* — Tarolli, Sundheim, Covell & Tummino LLP (57) ABSTRACT

A method of diagnosing a mitochondrial related disease in a subject includes administering a deuterated metabolic water precursor to the subject, measuring a rate of deuterated water formation in a sample region of the subject, and comparing the measured deuterated water formation in the sample region to a control value. A difference between the rate of deuterated water formation in the sample region compared to a control value is indicative of a mitochondrial related disease.

4 Claims, 5 Drawing Sheets

DEUTERATED METABOLIC WATER PRECURSOR FOR DETECTING AND TREATING DISEASED TISSUE

RELATED APPLICATION

This application claims priority from U.S. Provisional Application No. 61/218,732, filed Jun. 19, 2009, the subject matter which is incorporated herein by reference.

BACKGROUND

Deuterium, also called heavy hydrogen, is a stable naturally occurring (0.015%) isotope of hydrogen. A deuteron, the nucleus of deuterium, contains one proton and one neutron, whereas the far more common 'light' hydrogen nucleus contains no neutrons. Deuterium can be used as a non-radioactive, stable isotopic tracer since small concentrations of heavy water are nontoxic in most organisms. The adult human body naturally contains deuterium equivalent to the amount in about 5 grams of heavy water. In chemical reactions and metabolic pathways, deuterium behaves similarly to ordinary hydrogen, but it can be distinguished from ordinary hydrogen by its mass, using mass spectrometry or infrared spectrometry.

Owing to its tracer qualities, Deuterium is especially useful in deuterium nuclear magnetic resonance spectroscopy (DMR). Deuterium's nuclear spin properties, which differ from those of light hydrogen usually present in organic molecules, allow deuterated organic compounds to be detected with great sensitivity using DMR. Such compounds, including deuterated water (e.g., HDO), are widely used in studies related to metabolism and the movement of drugs and toxic substances in humans and other animals.

Mitochondria are the organelles of oxidative phosphorylation and are present in nearly all eukaryotic cells. A change in cellular oxidative demand can reduce the metabolic rate of oxygen consumption in a particular tissue. Therefore, the mitochondrial metabolic rate of oxygen consumption has profound implications for human health in relation to mitochondrial disease and disorders.

Magnetic resonance spectroscopy utilizing heavy isotope labeled oxygen, such as $^{17}$O-MR, has been used to determine the metabolic rate of oxygen consumption ($MRO_2$). For example, it has been shown that $^{17}$O-MR makes it possible to determine directly and non-invasively the metabolic rate of oxygen consumption in a sample via the quantitative measurement of the nascent $^{17}$O labeled mitochondrial water. The highly exergonic redox reaction that leads to nascent mitochondrial water provides the energy incorporated in ATP. If the breathing air is enriched in $^{17}O_2$, the resulting $H_2^{17}O$ can be quantitatively measured and related to $MRO_2$ (Mateescu and Cabrera, (1997) Adv Exp Med Biol. 411:585-590).

$^{17}$O-MR constitutes an excellent avenue for monitoring oxygen consumption. However, it would be advantageous to add the possibility of also measuring $MRO_2$ through the influx of protons provided by food (e.g., sugars, fat, proteins, etc.) in order to determine the metabolic rate of oxygen consumption in a sample.

SUMMARY

The present invention generally relates to a method and system for diagnosing a mitochondrial related disease or disorder in a subject as well as a method of inducing apoptosis in a diseased cell of an organism or person with at least one pathology.

In one aspect of the present invention, a method of diagnosing a mitochondrial related disease in a subject includes the steps of: (1) administering an amount of deuterated metabolic water precursor to the subject; (2) determining a rate of deuterated water formation in a sample region; and (3) comparing the rate of deuterated water formation in the sample region to a control value. The difference between the rate of deuterated water formation in the sample region compared to a control value is indicative of a mitochondrial related disease.

Another aspect of the invention relates to a system for determining the metabolic rate of oxygen consumption in a sample or sample region. The system includes a deuterated metabolic water precursor, an imaging device for detecting deuterated mitochondrial water formed by administration of the deuterated metabolic water to a subject, and an imaging logic for measuring the formation of the deuterated mitochondrial water formed in the subject.

In an aspect of the invention the imaging logic can include at least one of: (1) input logic for measuring the baseline deuterated water content in a sample or sample region; (2) input logic for measuring the deuterated water content in the sample after administration of deuterated metabolic water precursor molecules; (3) input logic for determining the rate of deuterated water formation in the sample or sample region; or (4) input logic for determining the rate of $MRO_2$ in the sample.

Yet another aspect of the invention relates to a method of inducing apoptosis in a diseased cell of an organism with at least one pathology. The method includes administering to the cell an amount of a isotopically labeled metabolic water precursor effective to produce a mitochondrial isotope effect stress in the cell leading to apoptosis of the cell. In some aspects, the administration of an isotopically labeled metabolic water precursor to the cell reduces cellular proliferation. This effect is enhanced by the fact that the isotope effect is concentrated in mitochondria. In certain aspects of the invention, the isotopically labeled metabolic water precursor is deuterated glucose.

In another aspect of the invention, a method of treating a mitochondrial related disease in a subject is provided. The method includes administering to the subject a therapeutically effective amount of an isotopically labeled metabolic water precursor molecule. In some aspects of the invention, the administration of the isotopically labeled metabolic water precursor molecule to the subject can produce a mitochondrial isotope effect stress in a diseased cell of a subject leading to apoptosis of the cell. In some aspects, the administration of an isotopically labeled metabolic water precursor to the subject reduces cellular proliferation in the subject. In certain aspects of the invention, the isotopically labeled metabolic water precursor is deuterated glucose.

In other aspects, the isotopically labeled metabolic water precursor molecule can be administered to subject in combination in combination with isotopes of oxygen to enhance the mitochondrial isotope effect stress. In one example, the isotopically labeled metabolic water precursor molecule can be deuterated glucose that is administered to the subject by parenteral or enteral administration and the isotope of oxygen is $^{17}O_2$ that is administered to the subject by inhalation.

DETAILED DESCRIPTION

The present invention generally relates to a method and system for diagnosing a mitochondrial related disease or disorder in a subject as well as a method of inducing apoptosis in a diseased cell of an organism with a disease, disorder, or pathology. Mitochondrial functions, including both oxygen respiration and the glucose metabolic pathways, converge into a final, highly exergonic reaction of water formation. It was found that administration to a subject of isotopes of metabolic precursor molecules of water, such as deuterated glucose, to a subject results in the formation of deuterated metabolic water (D$_2$O and/or HDO) in mitochondria. The rate of deuterated water formation in a sample from or sample regions of a subject can be directly measured by deuterium magnetic resonance (DMR). Measurement of deuterated water formation can be used determine the metabolic rate of oxygen (MRO$_2$) consumption in samples or sample regions of the subject without employing $^{17}$O enriched air and, thus, used to measure mitochondrial function and/or aberrant mitochondrial function in a sample or sample region of the subject.

One aspect of the present invention relates to a method of diagnosing a disease or disorder associated with aberrant mitochondrial function in a subject by administering a deuterated metabolic water precursor to a subject and measuring the rate deuterated water formation in a sample or sample region of the subject. The measured rate of deuterated water formation as well as the amount or level of deuterated water formed can be correlated with or compared to a control value, rate, or level to determine aberrant mitochondrial function in the sample region of the subject and the presence or absence of a pathology or disorder associated with aberrant mitochondrial function. An increase or decrease in the rate or level of deuterated water formation compared to the control is value is indicative of aberrant mitochondrial function.

The deuterated metabolic water precursor can be any organic deuterated metabolic water precursor molecule that is metabolized in the body to form a deuterated metabolic water molecule. The deuterated metabolic water percursor can contains a deuterium-containing compound together with a physiologically tolerable diluent. The deuterium-containing compound is contemplated to be a physiologically compatible, metabolizable deuterated compound and includes foods that contain, deuterated sugars, fatty acids, proteins, amino acids, lipids, nucleotides, and carbohydrates. Such foods contain physiologically compatible, metabolizable deuterated compounds produced either synthetically or by the growth of natural organisms, such as plants, molds, bacteria, algae, plankton, and the like, in deuterium-enriched water. Specific illustrative deuterated foods are fruit, e.g., apples, oranges, and the like, and vegetables, e.g., potatoes, carrots, beets, and the like.

Figure 3:
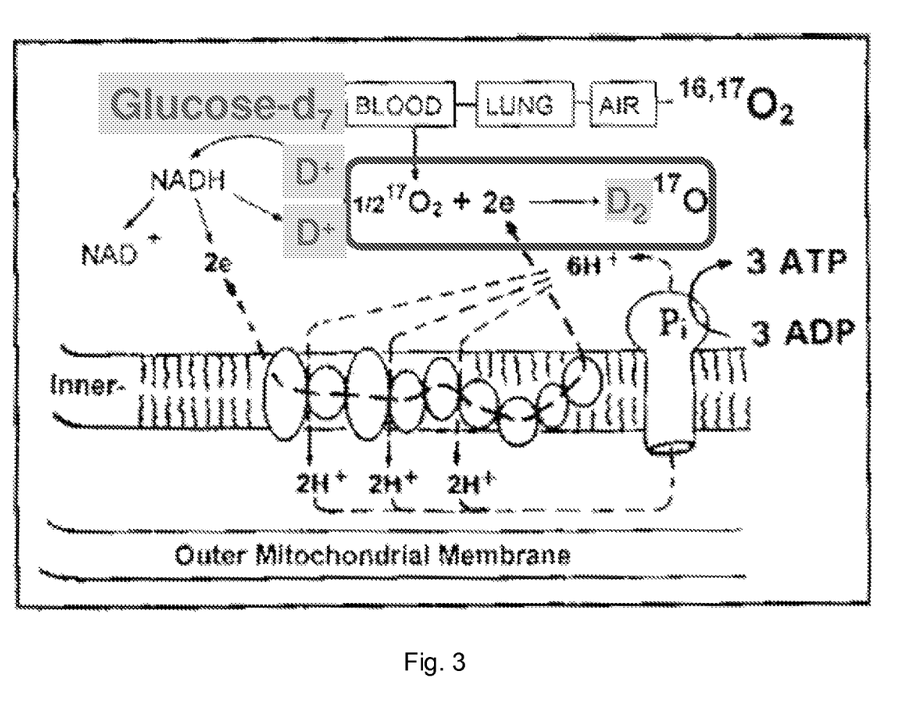
FIG. 3 illustrates deuterated glucose metabolized by mitochondria to deuterated water.

In one particular example, the deuterated metabolic water precursor includes deuterated glucose. As illustrated in FIG. 3, deuterated glucose is metabolized by mitochondria to deuterated water. Oxidation via the citric acid cycle ensures that all deuterium atoms are released to deuterated water. In certain aspects of the invention, the deuterated metabolic water precursor is deuterated glucose that can be administered by ingestion (e.g., by drinking) or by injection (intravenous or intraperitoneal). The deuterated glucose can be deuterated at different positions. For example, the deuterated glucose of the present invention can include [6,6-2H2] glucose, [1-2H]glucose, and D-7 Glucose[1,2,3,4,5,6-2H7].

In some aspects, a deuterated sugar may be fructose or galactose. Fructose is metabolized via the fructose 1-phosphate pathway, and secondarily through phosphorylation to fructose 6-phosphate by hexokinase. Galactose is metabolized via the galactose to glucose interconversion pathway. Any other sugar may be utilized in the disclosed methods. Other monosaccharides, include, but are not limited to, trioses, pentoses, hexose, and higher order monosaccharides. Monosaccharides further include, but are not limited to, aldoses and ketoses.

In some aspects, compositions including deuterated polysaccharides may be administered to the subject. The polymers may be formed from monosaccharides. For example, deuterated glycogen, a polysaccharide, is formed by deuterated glucose residues. In further aspects, deuterated sugar monomers may be administered as a component of sucrose (glucose α-(1,2)fructose), lactose (galactose-(1,4)-glucose), maltose (glucose α-(1,4)-glucose), starch (glucose polymer), or other polymers.

Diseases or disorders associated with mitochondrial function can be diagnosed and treated by the methods described herein include degradative or degenerative diseases, such as mitochondrial related diseases, or any disease that results in the perturbation of the normal function of tissue and organ cells.

As used herein, the term "mitochondrial related disease" refers to a disease, condition, or disorder where the function of the mitochondria is disrupted. The function can be disrupted by mitochondrial DNA (mtDNA) damage, proteins functioning abnormally within the mitochondria, membrane depolarization, and the like. A "mitochondrial related disease" can also be referred to as an energy-loss disease because the mitochondria supply the energy for the cell. A "mitochondrial related disease" can also be referred to as a premature cell death disease because loss of the mitochondrial energy supply can initiate necrosis or control the release of pro-apoptotic proteins into the cytoplasm.

In one aspect of the invention, the mitochondrial related disease is associated with the degradative (oxidative) functions of mitochondria. Mitochondrial related disease may include MELAS (Mitochondrial encephalomyopathy with lactic academia and stroke-like episodes), MERRF (Myoclonus, epilepsy, and myopathy with ragged red fibers), NARP/MILS (Neurogenic muscular weakness, ataxia, retinitis pigmentosa/Maternally inherited Leigh syndrome), LHON (Lebers hereditary optic neuropathy) "Mitochondrial blindness", KSS (Kearns-Sayre Syndrome), PMPS (Pearson MarrowPancreas Syndrome), CPEO (Chronic progressive external opthalmoplegia), Leigh syndrome, Alpers syndrome, Multiple mtDNA deletion syndrome, MtDNA depletion syndrome, Complex I deficiency, Complex II (SDH) deficiency, Complex III deficiency, Cytochrome c oxidase (COX, Complex IV) deficiency, Complex V deficiency, Adenine Nucleotide Translocator (ANT) deficiency, Pyruvate dehydrogenase (PDH) deficiency, Ethylmalonic aciduria with lactic acidemia, 3-Methyl glutaconic aciduria with lactic acidemia, Refractory epilepsy, Asperger syndrome with declines during infection, Autism, Attention deficit hyperactivity disorder (ADHD), Cerebral palsy, Dyslexia, materially inherited thrombocytopenia and leukemia syndrome, MNGIE (Mitrochondrial myopathy, peripheral and autonomic neuropathy, gastrointestinal dysfunction, and epilepsy), MARIAHS syndrome (Mitrochondrial ataxia, recurrent infections, aphasia, hypouricemialhypomyelination, seizures, and dicarboxylic aciduria), ND6 dystonia, Cyclic vomiting syndrome, 3-Hydroxy isobutryic aciduria with lactic acidemia, Diabetes mellitus with lactic acidemia, Uridine responsive neurologic syndrome (URNS), Familial Bilateral Striatal Necrosis (FBSN), Aminoglycoside-associated deafness, Dilated cardiomyopathy, Splenic Lymphoma, Wolfram syndrome, Multiple mitrochondrial DNA deletion syndromes, and Renal Tubular AcidosislDiabetes/Ataxis syndrome.

A mitochondrial disease, as contemplated by the present invention, can include multifactorial forms of mitochondrial disease including much more common disorders, such as Huntington's disease, Parkinson's disease, Alzheimer's disease, and even certain forms of diabetes, heart disease, migraine, and stroke. Indeed the process of aging itself has been linked to progressive declines in mitochondrial function.

In some aspects of the invention, the diseases and disorders diagnosed and treated by the present invention can include diseases and disorders related to aberrant glucose metabolism. Aberrant glucose metabolism can include both increased and decreased glucose metabolism compared to healthy samples or sample regions. It is well established that tumor cells have altered glucose metabolism. Cancerous tissue is known to consume 20-30 more glucose compared to normal tissue. To accomplish the high metabolic rate, there is upregulation of glucose transporter (Glut 1-4), hexosekinase, and glucose 6 phosphatase. Therefore, in one particular example, a disease characterized by an increase in glucose metabolism is cancer. In another particular example, a disease characterized by a decrease in glucose metabolism can include an ischemia, such as, but not limited to a cardiac ischemia, brain ischemia, ocular ischemia, or mesenteric ischemia.

Figure 1:
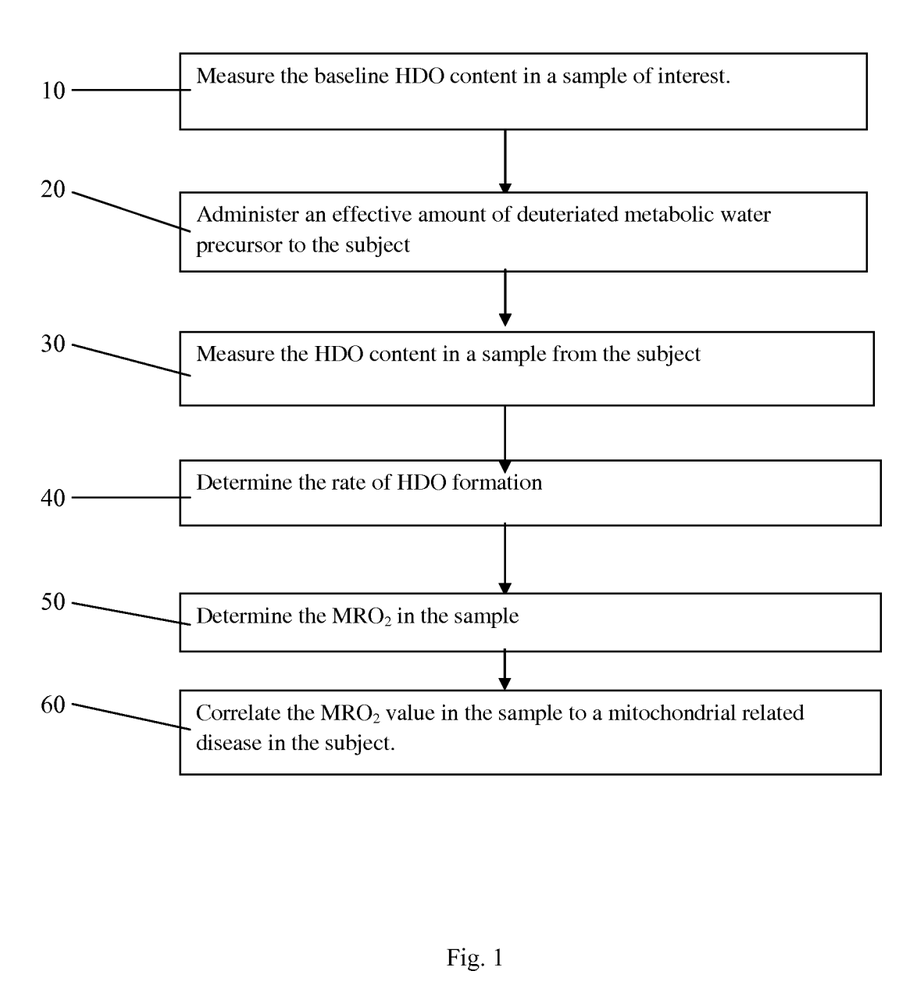
FIG. 1 is a flow diagram illustrating a method of diagnosing a mitochondrial related disease in a subject.

FIG. 1 is a schematic flow diagram illustrating a method of detecting a mitochondrial disease or disorder in a subject in accordance with one aspect of the invention. As shown in block 10 of FIG. 1, the method includes measuring a baseline deuterated water content in a sample or sample region of interest. The step of measuring the baseline deuterated water content in the sample or sample region of interest can include using a nuclear magnetic resonance (NMR) spectrometer to acquire control image data sets of deuterated water. It has been demonstrated that nuclear magnetic resonance imaging of deuterium can be used in vivo to detect deuterated water in mammals. Ewy et al., MRM Volume 8, Issue 1, pages 35-44 (1988). In one particular example, included below as Example 1, a subject can be placed in a NMR tube or cradle for obtaining the DMR spectrum. In certain aspects of the invention, the DMR measurements may be performed on a NMR microimager equipped with a multinuclear probe.

The control image data sets can correspond to a control value, such as a spectrum of natural abundance of deuterated water from the sample or sample region of interest prior to administration of a deuterium labeled metabolic water precursor. The control image data sets that are acquired prior to injection of the deuterium labeled metabolic water precursor are used to determine a baseline or control deuterated water level of the sample or sample region of interest.

A sample, as contemplated by the present invention can include a cell sample, a tissue sample, an organ, a region of an organ, a region of a tissue, or any other region of interest from a subject. The subject may be a mammal, preferably a mammalian subject that is suspected of having a mitochondrial related disease or disorder. The sample may include growing tissues, such as muscle, liver, adrenal tissue, prostate tissue, colon tissue, endometrial tissue, skin, breast tissue, adipose tissue, or other tissue capable of somatic growth. In some aspects, the sample may be or include tumor cells. In some aspects, the subject may be starved for an amount of time (e.g., 12-24 hours) prior to the measuring the baseline deuterated water content in a sample or sample region of interest.

As shown in block 20 of the flow diagram of FIG. 1, the method further includes administering an effective amount of deuterated metabolic water precursor to a subject. The amount of deuterated metabolic precursor can be established based on known consumption data; however, a set of concentrations may be established if necessary. Deuterated metabolic water precursors may be administered orally, by gavage, intraperitoneally, intravascularly including intraarterially and intravenously, subcutaneously, or other bodily routes. In particular, the deuterated metabolic water precursors may be administered to an individual orally, optionally as part of a food or drink. By "administering" or "administration" is meant any method that introduces the deuterated precursor to, in or on a subject.

The deuterated metabolic precursor molecule may be administered to a subject for a period of time sufficient for the label of the deuterated metabolic water precursor molecule to be completely consumed by the subject. The period of time may be a pre-determined length of time. This period of time may be determined a priory by DMR measurements.

As shown in block 30 of the flow diagram of FIG. 1, following administration of the deuterated metabolic water precursor, the method further includes the step of measuring the deuterated water content of a subject sample or sample region by localized DMR. The step of measuring the deuterated water content in a subject sample includes acquiring DMR image data sets of deuterated water in a sample or sample region post deuterated metabolic water precursor administration. The "post-administered" or "post" DMR image data sets, as defined herein, are the DMR image or spectral data sets that are acquired immediately after administration of the deuterated metabolic water precursor is initiated.

A series of DMR image data sets are acquired throughout the administration of a deuterated metabolic water precursor. The step can also include acquiring DMR image data sets of deuterated water for a sufficient amount of time thereafter to determine the rate of deuterated water production in the sample or sample region. In order to determine the quantity of deuterated water in a sample, analysis software can be used to interpret in a quantitative manner the size of spectrum peaks provided by the DMR image data sets. Quantitative measurements are performed on two well separated peaks of deuterated water and deuterated fat.

Once the metabolic deuterated water content of the sample is measured, the rate of deuterated water production can be determined, as shown in block 40 of FIG. 1. The deuterated water production rate may be calculated by combinatorial analysis, by hand or via an algorithm. The rate of metabolic deuterated water formation may be calculated using the baseline (natural abundance) deuterated water content of the sample and the deuterated water content of the sample post administration in order to determine the fraction of nascent mitochondrial deuterated water post administration. In one example, the change in the fraction of nascent mitochondrial deuterated water over time in a sample or sample region can be used to calculate the rate of production of metabolic water.

As shown in block 50 of FIG. 1, the rate of metabolic water formation can be used to further calculate the metabolic rate of oxygen consumption ($MRO_2$) in the sample or sample region. The $MRO_2$ may be calculated by combinatorial analysis, by hand or via an algorithm. A summary of the quantification of $MRO_2$ is described in Mateescu et al., Adv Exp Med Biol. 411:585-590 (1997), which is incorporated herein by reference.

As shown in block 60 of FIG. 1, the method further includes the step of correlating the $MRO_2$ value in the sample or sample region to one or more mitochondrial related diseases or disorders. It is contemplated by the present invention that the difference in $MRO_2$ value in the sample compared to a control $MRO_2$ value may be indicative of the subject having a mitochondrial related disease.

The control $MRO_2$ value can be derived using the methods described above. In some aspects of the invention, the control $MRO_2$ level can be determined in a healthy sample or sample region from the same subject as a subject sample (e.g., a tissue suspected of having a mitochondrial related disease or disorder). Alternatively, the $MRO_2$ value of one or more subject samples may be measured and compared at two or more different times. It is also contemplated that the control $MRO_2$ level can be derived concurrently with the subject sample or sample region. For example, a practitioner may compare a suspected healthy sample region of a subject and a suspected diseased sample region concurrently.

The control $MRO_2$ value can also include a $MRO_2$ value derived from a control population of healthy individuals. For example, the relative aerobic $MRO_2$ of mitochondria in a first population of tissues or individuals that lack a mitochondrial related disease or disorder are measured and compared. The relative $MRO_2$ of the mitochondria in a second population of one or more tissues or individuals are measured and compared. A difference between the $MRO_2$ value between the first and the second populations is then identified and used to detect, prognose, or monitor the progression of a mitochondrial related disease or disorder.

By way of example, the method of the present invention can be used to detect and/or measure aberrant cell growth and/or neoplastic cell growth and proliferation associated with cancer. As discussed above, cancerous tissue is known to consume 20-30 more glucose compared to normal tissue. In accordance with the diagnostic method, deuterated glucose can be administered to a subject. The rate and/or amount of deuterated mitochondrial water produced by a region, tissue, or cells of the subject suspected of having cancer can then be measured using DMR. The measured rate or level of deuterated water produced by the region, tissue, or cells can then be compared with a control rate or level to determine if the region, tissue, or cells exhibit enhanced mitochondrial deuterated water production indicative of neoplastic cell growth or cancer. In some examples of the invention, the control rate or level of deuterated mitochondrial water production can be the rate or level of a comparable or similar region, tissue, or cells in the subject that is generally healthy or free of neoplastic cell growth or cancer.

In other examples of the invention, the control rate or level of deuterated mitochondrial water production can be a rate of deuterated mitochondrial water product in the region, tissue, or cells measured at an earlier date.

The diagnostic method of the present invention can be used for not only diagnosing the presence of a mitochondrial related disease, but also for measuring the efficacy of a therapy in treating a mitochondrial related disorder. Another aspect of the invention, therefore, relates to a method of monitoring the efficacy of a therapy for treating a mitochondrial related disease. The method can include administering a deuterated metabolic water precursor to the subject prior to or during a therapy of a subject and determining the amount or rate of deuterated water formation in the tissue treated. After therapy or subsequent to the initial deuterated metabolic precursor water measurement, a similar dosage of deuterated metabolic water precursor can be administered to the subject, and the amount or rate of deuterated water formation in the tissue treated can be determined. Comparison of initial amount or rate of deuterated water formation with the later measured amount or rate of deuterated water formation can be indicative of the efficacy of the therapy.

In another aspect of the invention, the deuterated metabolic water precursor may be used in an in vitro method, e.g., to contact a culture of cells or tissue. In this variation, the method for determining the $MRO_2$ in the cultured cells or tissue includes: 1) measuring the baseline deuterated water content of the cells or tissue; 2) contacting the cell or tissue with deuterated metabolic water precursor; 3) measuring the deuterated water content; 4) determining the rate of deuterated water production in the cells or tissue; and 5) determining the $MRO_2$ of the cells or tissue. The $MRO_2$ of the sample can then be compared to a reference value representing the $MRO_2$ in a healthy control sample and correlated to a mitochondrial disease or disorder as described above.

The cells or tissues used in an in vitro method described above may be obtained, for example, by blood draw, urine collection, biopsy, or other methods known in the art. The samples may be one or more biological fluids. Samples may also be obtained from specific organs or tissues, such as muscle, liver, brain tissue, kidney tissue, adrenal tissue, prostate tissue, endometrial tissue, blood, skin, and breast tissue. The sample may be from a specific group of cells, such as tumor cells or fibroblast cells. The samples may be obtained pre-mortem or post-mortem.

In one particular example, a cell sample may be obtained from a subject. The baseline deuterated water content of the cells is measured. The cells are then contacted with a deuterated metabolic water precursor, such as deuterated glucose. Then the deuterated water content of the cells is measured. Using the baseline deuterated water content and the deuterated water content of the cells post deuterated water administration, the rate of deuterated water formation in the cells is determined. Using the rate of deuterated water formation, the metabolic rate of oxygen formation is then determined. Finally, the metabolic rate of oxygen consumption in the cells can be compared to the metabolic rate of oxygen consumption of cells obtained from a similar site in the same subject. An increased metabolic rate of oxygen consumption in the cell sample compared to the cells of a similar site is associated with cancer.

The present invention also relates to a system for diagnosing a mitochondrial related disease. The system can include a deuterated metabolic water precursor, an imaging device for measuring deuterated water formation following administration of the deuterated metabolic water precursor molecule to a subject and an imaging logic for determining at least one of image data set analysis, deuterated water quantitative analysis, the rate of deuterated water formation analysis, and $MRO_2$.

The imaging device of the system can include a magnetic resonance apparatus. The apparatus can include a basic field magnet and by a basic field magnet supply. The system can have gradient coils for emitting the desired gradient magnetic fields, operated by a gradient coil supply. A radio frequency (RF) antenna can be provided for generating the RF pulses, and for receiving the resulting magnetic resonance signals from an object being imaged. The RF antenna can be operated by an RF transmission/reception unit. The gradient coil supply and the RF transmission/reception unit are operated by a control computer to produce radio frequency pulses, which are directed to the sample to be imaged. The magnetic resonance signals received from the RF antenna can be subject to a transformation process, such as a two-dimensional fast Fourier Transform, which generates pixilated image data. The transformation can be performed by an image computer or other similar processing device. The image data may then be shown on a display.

Figure 2:
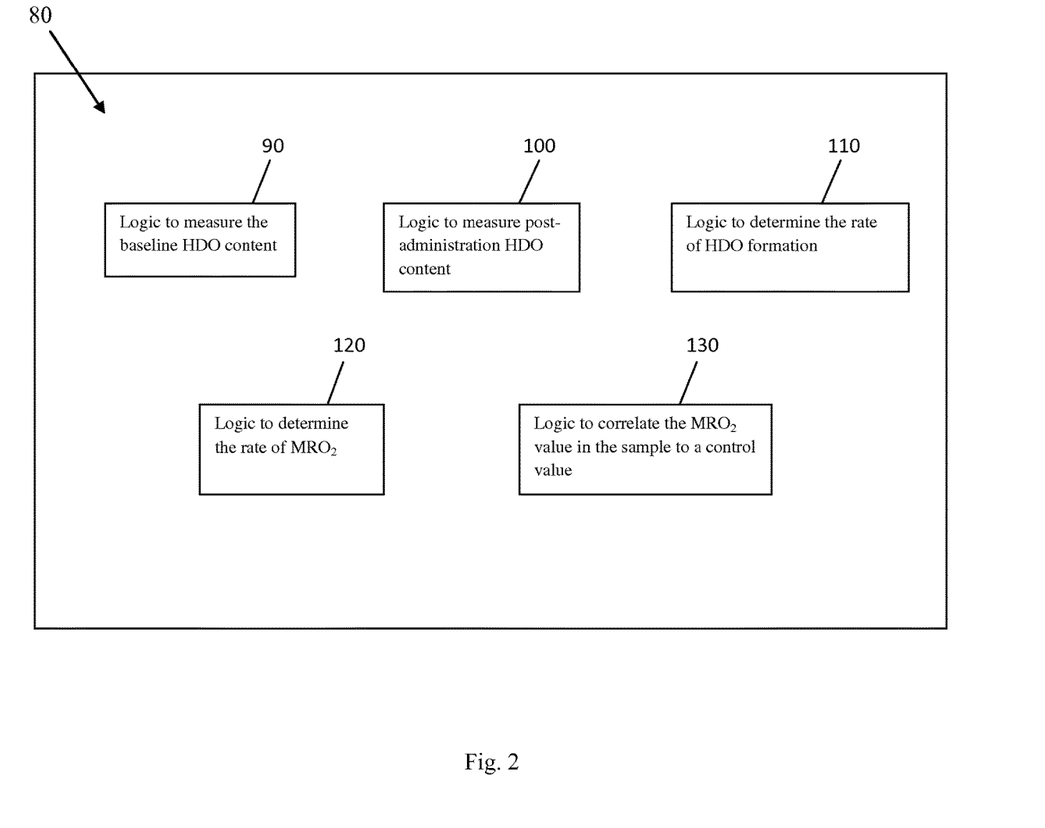
FIG. 2 is a schematic illustration of an imaging logic for determining the MRO$_2$ in a sample.

FIG. 2 is a schematic illustration of the imaging logic of the system. Rectangular elements in FIG. 2 denote "processing blocks" and represent computer software instructions or groups of instructions. The processing blocks can represent steps performed by functionally equivalent circuits, such as a digital signal processor circuit or an application specific integrated circuit (ASIC). The image logic does not depict syntax of any particular programming language. Rather, the image logic illustrates the functional information one skilled in the art may use to fabricate circuits or to generate computer software to perform the processing of the system. It should be noted that many routine program elements, such as initialization of loops and variables and the use of temporary variables are not shown.

The imaging logic may be implemented as software executable by one or more computers or other processing devices. It may be embodied in a computer readable medium, such as a magnetic disk, digital compact disk, electronic memory, persistent and/or temporary memories, and other types of memories as known in the art. It will be appreciated that electronic and software applications involve dynamic and flexible processes such that the illustrated blocks can be performed in sequences other than the one shown. It will also be appreciated by one of ordinary skill in the art that elements embodied as software may be implemented using various programming approaches such as machine language, procedural, object oriented or artificial intelligence techniques.

Referring to FIG. 2, the image logic 80 of the present invention can include input logic 90 for measuring the baseline deuterated water content in a sample or sample region prior to the administration of deuterated metabolic water precursor, logic 100 for measuring the deuterated water content in a sample or sample region post-administration of deuterated metabolic water precursor, input logic 110 for determining the rate of deuterated water formation in the sample or sample region from the deuterated water quantitations, logic 120 for determining the $MRO_2$ in the sample or sample region from the rate of deuterated water formation. The system 80 further may further comprises logic 130 to correlate the $MRO_2$ value in the sample to a control value.

The flow diagram of FIG. 1 represents an example of a methodology that can be performed or implemented using the system. As illustrated, the steps of FIG. 1 represent functions, actions and/or events performed therein to diagnose or detect the presence of mitochondrial related disease in a subject using the deuterated metabolic water precursor, an imaging device, and the imaging logic of the system.

Another aspect of the present invention relates to a method of inducing apoptosis in diseased cell of an organism or a subject with a disease, disorder, and/or pathology by administering to the subject a therapeutically effective amount of an isotopically labeled metabolic water precursor. It has been shown, for example, that $D_2O$ is more toxic to malignant cells than normal animal cells. (Kushner et al. Pharmacological uses and Perspectives of heavy water and deuterated compounds, Can. J. Physiol. Pharmacol. 77, 79-88 (1999)). Deuterated water formed upon administration of an isotopically labeled metabolic water precursor along with the combined kinetic isotope effect of, for example, $^2H$, $^{17}O$, $^{18}O$ and/or $^{13}C$ on vital enzymatic reactions can produce a local stress that can be overcome by normal healthy cells, but not by diseased cells. This can be due to the fact that the effective processes are specifically occurring in the mitochondria.

An isotopically labeled metabolic water precursor, as used herein, is any isotope of an organic molecule that can be metabolized in the body by mitochondria or incorporated into a mitochondrial molecule in a living system. The isotopically labeled metabolic water precursor can include but is not limited to deuterated labeled sugars, fatty acids, proteins, amino acids, lipids, nucleotides, and carbohydrates.

In one aspect of the invention, the isotopically labeled metabolic water precursor can be an isotopically labeled sugar. In some aspects, the isotopically labeled sugar can be isotopically labeled with deuterium and/or $^{13}C$. In particular aspects, the isotopically labeled sugar is deuterated glucose or deuterated glucose precursors.

Cells of organisms administered an isotopically labeled metabolic precursor molecule may experience a mitochondrial isotope effect stress due to the kinetic isotope effect on the enzymatic reactions of cellular life processes. The kinetic isotope effect (KIE) is a dependence of the rate of a chemical reaction on the isotopic identity of an atom in a reactant. A ME involving hydrogen and deuterium is represented as:

$$KIE = \frac{k_H}{k_D}$$

with $k_H$ and $k_D$ reaction rate constants.

It is known that isotopic substitution can modify the rate of reaction in a variety of ways. In many cases, the rate difference is explained by the mass of an atom affecting the vibration frequency of the chemical bond that it forms, even if the electron configuration is nearly identical. Typically, heavier atoms will lead to lower vibration frequencies, or, viewed quantum mechanically, will have lower zero-point energy. With a lower zero-point energy, more energy must be supplied to break the bond, resulting in a higher activation energy for bond cleavage, which in turn lowers the measured rate.

An isotopic substitution will greatly modify the reaction rate when the isotopic replacement is in a chemical bond that is broken or formed in the rate limiting step. In such a case, the change is termed a primary isotope effect. When the substitution is not involved in the bond that is breaking or forming, a smaller rate change, termed a secondary isotope effect is observed. Isotopic rate changes are most pronounced when the relative mass change is greatest since the effect is related to vibrational frequencies of the affected bonds. For example, changing a hydrogen atom (H) to deuterium (D) represents a 100% increase in mass, whereas in replacing carbon-12 with carbon-13, the mass increases by only 8%. The rate of a reaction involving a C—H bond can be 6 to 10 times faster than the corresponding C-D bond, whereas a 12C reaction is only ~1.04 times faster than the corresponding 13C reaction (even though, in both cases, the isotope is one atomic mass unit heavier).

Diseased cells are less resistant to isotopic stress than healthy cells. The kinetic isotope effect of deuterium and other isotopes on enzymatic reactions is expected to produce a strong and highly localized mitochondrial stress that will be overcome by healthy cells, but not by diseased cells. Normal healthy cells of tissues and organs may be resistant to the biochemical and physiological stress caused by the kinetic isotope effect, while the diseased cells will become apoptotic and will be eventually eliminated from the affected organism. Thus, administration of an isotopically labeled metabolic water precursor molecule to a cell can produce mitochondrial isotope effect stress in the cell leading to apoptosis of the diseased cell.

A therapeutically effective amount is the quantity of the isotopically labeled metabolic water precursor sufficient to reduce, prevent, ameliorate, or completely avoid signs and symptoms of mitochondrial disorders in the subject. Depending on the solubility of the particular formulation of isotopically labeled metabolic precursor molecule administered, the daily dose to ameliorate signs and symptoms of mitochondrial disorders may be divided among one or several unit dose administrations. As those of skill in the art will understand, the dosages can be tailored to the individual subject's needs by an appropriate treating health care professional, taking into account the subject's age, weight, size, condition, and the like.

In one example, a therapeutically effective amount of isotopically labeled metabolic water precursor administered to the subject is an amount of an isotopically labeled metabolic water precursor molecule effective to induce apoptosis in unhealthy cells. In another example, a therapeutically effective amount of isotopically labeled metabolic water precursor administered to the subject is an amount of an isotopically labeled metabolic water precursor molecule effective to slow down cellular proliferation processes such as those in tumors or cancer.

The isotopically labeled metabolic water precursor can be administered to the subject by parenteral, enteral, or topical administration. Examples of such administration can include intravenous administration as well as oral consumption of the isotopically labeled metabolic water precursor.

In another aspect of the invention, isotopes of oxygen can be topically administered to the subject by inhalation concomitantly with administration of the isotopically labeled metabolic water precursor, such as deuterated glucose or a deuterated glucose precursor, to increase the isotopic stress used to treat the mitochondrial related disease. For example, $^{17}O_2$ and/or $^{18}O_2$ can be co-administered with deuterated glucose to increase the isotopic stress on the unhealthy cells.

The following example is offered to illustrate, but not to limit, the claimed invention.

EXAMPLE

Figure 4:
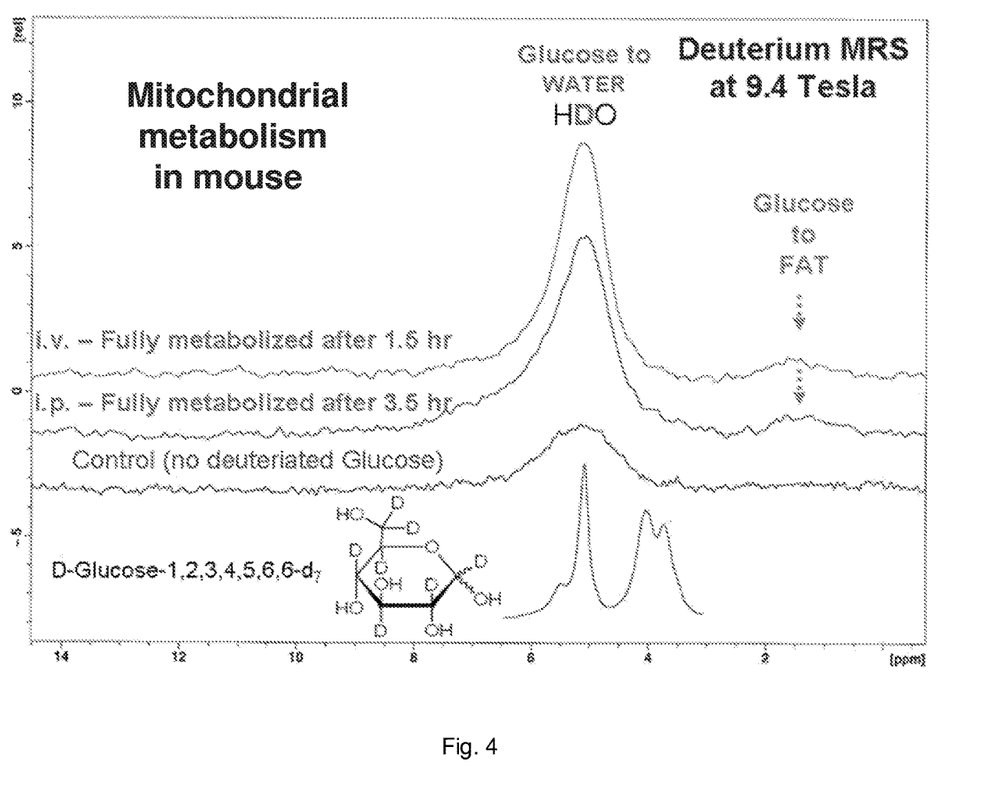
FIG. 4 illustrates an NMR spectrum for the mitochondrial metabolism in mice.
Figure 5:
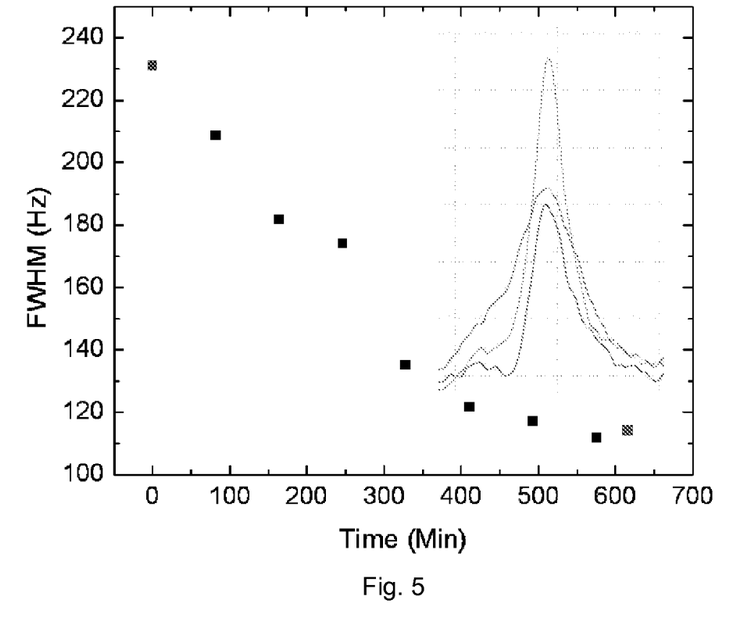
FIG. 5 illustrates a $^2$H spectra together with a graph that displays the time evolution of the spectral line width for Tenebrio molitor larvae starved for several days, then placed in a 20 mm NMR tube together with food consisting of 0.4 g bran wetted with an aqueous solution of deuterated glucose.
Figure 6:
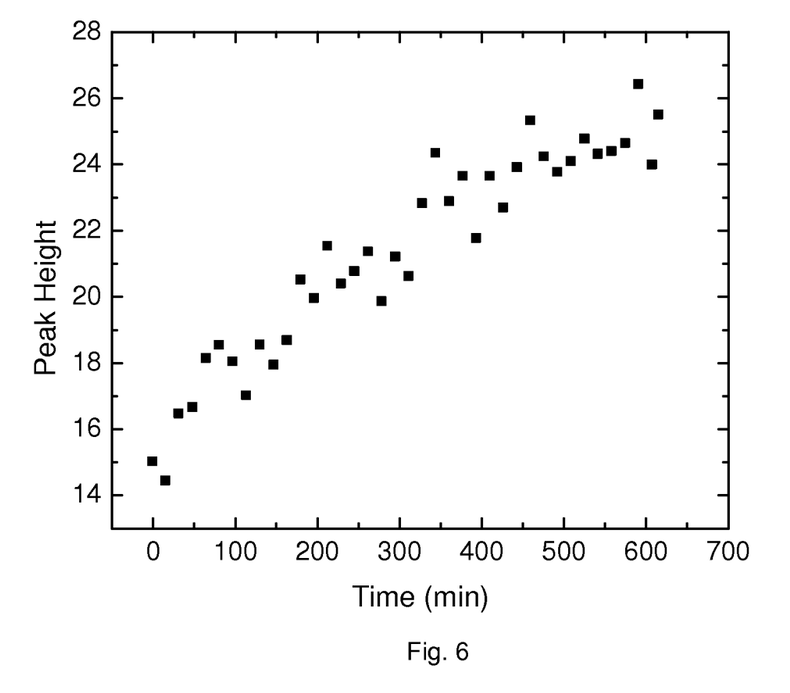
FIG. 6 illustrates the metabolic rate of HDO formation in Tenebrio molitor larvae.

DMR measurements (AQ 0.2s; TR 0.3s; NS 128; LB 30; 38s/spectrum) were performed at 9.4 T on a wide bore (89 mm) Bruker Avance microimager equipped with a multinuclear probe. A set of experiments was performed on three male mice (C57/BL6) and another set, on Tenebrio molitor larvae. Mouse 1 (25 g), was injected iv with 8.9 mg deuterated glucose (ISOTEC) dissolved in 0.4 ml saline solution; it was sacrificed after 1.5 hr and, after dissection, its whole body (except fur and skin) was placed in a 20 mm NMR tube for running the DMR spectrum (shown in FIG. 4, upper trace). Mouse 2, (32 g) injected ip with the same amount of glucose-d7 as mouse 1 was sacrificed after 3.5 hr, and yielded the spectrum seen in the same FIG. 4, second trace. Mouse 3, (26 g) yielded the control (natural abundance) spectrum shown in FIG. 4, third trace. Tenebrio molitor larvae were starved for several days, then placed in a 20 mm NMR tube together with food consisting of 0.4 g bran wetted with an aqueous solution of deuterated glucose. Typical $^2H$ spectra are shown in FIG. 5 together with a graph that displays the time evolution of the spectral line width (see Results and Discussion). The rate of metabolic deuterated water formation in larvae is shown in FIG. 6.

It was observed that all deuterated glucose was consumed by the mice. While most of it provided protons for the formation of metabolic water, part of it was metabolized into fat.

In our approach, the excellent tracer quality of deuterium (natural abundance 0.015%) is combined with the fact that only two well separated peaks are to be measured; that of nascent metabolic water, and that of the aliphatic chain of fatty acids. Thus, in spite of their large line widths (100-230 Hz) due to the electric quadrupole moment and unfavorable correlation times, the spectra can be interpreted in a quantitative manner. FIG. 5 shows the graph of the change of the $^2H$ spectral line width with the progression of deuterated glucose consumption. The traces shown in the inset represent the natural abundance deuterated water peak of larvae that were not fed with glucose (lower trace) and the spectrum obtained from larvae immediately after being placed in the presence of food (bran containing deuterated glucose)—middle trace. The upper trace was recorded at the end of the experiment, when all glucose was metabolized into deuterated water (hence a line width similar to that of natural abundance of deuterated water, but a much higher intensity due to the labeling of the nascent mitochondrial water). Interestingly, in contrast to mice, the larvae did not incorporate a visible amount of D-label into fat.

From the above description of the invention, those skilled in the art will perceive improvements, changes and modifications. Such improvements, changes and modifications within the skill of the art are intended to be covered by the appended claims. All patents, patent applications and publications cited herein are incorporated by reference in their entirety.

Having described the invention, the following is claimed:

1. A method of treating aberrant mitochondrial function associated with cancer or ischemia in a sample region in a subject comprising:
    administering deuterated glucose or deuterated glucose precursor to the subject;
    measuring directly and simultaneously in vivo by deuterium magnetic resonance (DMR), rates of deuterated water formation and deuterated glucose or deuterated glucose precursor consumption in the sample region within the subject, wherein measurement by DMR comprises acquiring DMR image data sets for the sample region;
    comparing the rates of measured deuterated water formation and deuterated glucose or deuterated glucose precursor consumption in the sample region to a control value to determine a rate of metabolic deuterated water formation, wherein a difference between the rates of measured deuterated water formation and deuterated glucose or deuterated glucose precursor consumption in the sample region compared to the control value is indicative of the aberrant mitochondrial function associated with the cancer or ischemia; and treating the subject having aberrant mitochondrial function with a therapy for the cancer or ischemia.

2. The method of claim 1, further comprising determining a metabolic rate of oxygen consumption in the sample region by: calculating the metabolic rate of oxygen consumption using the rate of metabolic deuterated water formation; and comparing the metabolic rate of oxygen consumption to a control value, wherein a difference between the metabolic rate of oxygen consumption in the sample region compared to the control value is indicative of the aberrant mitochondrial function.

3. The method of claim 2, wherein the metabolic rate of oxygen consumption is determined without administering $^{17}O_2$ to the subject.

4. The method of claim 1, wherein the therapy for the cancer of ischemia comprises inducing apoptosis in a diseased cell of the subject by administering a therapeutically effective amount of an isotopically labeled metabolic water precursor to the subject.

* * * * *